US011406677B2

(12) United States Patent
Gromeier et al.

(10) Patent No.: US 11,406,677 B2
(45) Date of Patent: *Aug. 9, 2022

(54) ONCOLYTIC POLIOVIRUS FOR HUMAN TUMORS

(71) Applicant: Duke University, Durham, NC (US)

(72) Inventors: Matthias Gromeier, Durham, NC (US); John H. Sampson, Durham, NC (US); Darell D. Bigner, Mebane, NC (US); Annick Desjardins, Durham, NC (US); Henry S. Friedman, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/016,699

(22) Filed: Sep. 10, 2020

(65) Prior Publication Data

US 2020/0405795 A1    Dec. 31, 2020

Related U.S. Application Data

(60) Continuation of application No. 16/505,771, filed on Jul. 9, 2019, now Pat. No. 10,799,543, which is a division of application No. 15/428,510, filed on Feb. 9, 2017, now Pat. No. 10,398,743, which is a division of application No. 14/646,233, filed as application No. PCT/US2013/071246 on Nov. 21, 2013, now abandoned.

(60) Provisional application No. 61/729,021, filed on Nov. 21, 2012.

(51) Int. Cl.
*A61K 35/768* (2015.01)
*A61K 9/00* (2006.01)
*A61K 41/00* (2020.01)
*A61K 45/06* (2006.01)
*A61K 51/08* (2006.01)
*A61N 5/10* (2006.01)
*C12N 7/00* (2006.01)

(52) U.S. Cl.
CPC .......... *A61K 35/768* (2013.01); *A61K 9/0085* (2013.01); *A61K 41/00* (2013.01); *A61K 45/06* (2013.01); *A61K 51/081* (2013.01); *A61N 5/10* (2013.01); *C12N 7/00* (2013.01); *C12N 2770/32611* (2013.01); *C12N 2770/32632* (2013.01); *C12N 2770/32671* (2013.01); *C12N 2770/32733* (2013.01); *Y02A 50/30* (2018.01)

(58) Field of Classification Search
None
See application file for complete search history.

(56) References Cited

U.S. PATENT DOCUMENTS

| 6,264,940 | B1 | 7/2001 | Gromeier et al. |
| 6,464,972 | B1 | 10/2002 | Gromeier et al. |
| 6,518,033 | B1 | 2/2003 | Gromeier et al. |
| 7,147,848 | B2 | 12/2006 | Gromeier et al. |
| 8,076,070 | B2 | 12/2011 | Chen et al. |
| 10,398,743 | B2* | 9/2019 | Gromeier .............. A61K 41/00 |
| 10,799,543 | B2* | 10/2020 | Gromeier ................. A61P 1/00 |

FOREIGN PATENT DOCUMENTS

| EP | 2922564 B1 | 7/2018 |
| JP | 2016-500108 A | 1/2016 |
| WO | 00/08166 A1 | 2/2000 |

OTHER PUBLICATIONS

Merrill et al. Neuro-Oncology 2004 vol. 6, pp. 208-216 (Year: 2004).*
http://en.wikipedia.org/wiki/Polio_vaccine; dated Jul. 16, 2012.
Yang et al., "Evaluation of IRES-mediated, cell-type-specific cytotoxicity of poliovirus using a colorimetric cell proliferation assay," J. Virol. Methods, Jan. 2009, 155(1):44-54.
Dobrikova et al., "Attenuation of Neurovirulence, Biodistribution, and Shedding of a Poliovirus: Rhinovirus Chimera after Intrathalamic Inoculation in Macaca fascicularis," Journal of Virology, Mar. 2012, vol. 86, No. 5, pp. 2750-2759.
Goetz et al., "Preparing an oncolytic poliovirus recombinant for clinical application against glioblastoma multiforme," Cytokine Growth Factor Rev., Apr-Jun. 2010, 21(2-3):197-203.
Dello et al., "Growth phenotypes and biosafety profiles in poliovirus-receptor transgenic mice of recombinant oncolytic poliolhuman rhinoviruses," Journal of Medical Virology, Feb. 2008, 80(2):352-9.
Ochiai et al., "Targeted Therapy for Glioblastoma Multiforme Neoplastic Meningitis with Intrathecal Delivery of an Oncolytic Recombinant Poliovirus," Clin Cancer Res, Feb. 15, 2006, 12(4), pp. 1349-1354.
Merrill et al., "Poliovirus receptor CD155-targeted oncolysis of glioma," Neuro-Oncology, Jul. 2004, pp. 208-217.
Office Action dated Mar. 4, 2016 in related Australian Application No. 2013347945.
Goetz et al., "Oncolytic poliovirus against malignant glioma," Future Virology, Sep. 2011, vol. 6, No. 9, pp. 1045-1058.
Dobrikova et al., "Recombinant Oncolytic Poliovirus Eliminates Glioma In Vivo Without Genetic Adaptation to a Pathogenic Phenotype," Molecular Therapy, Nov. 2008, vol. 16, No. 11, pp. 1865-1872.
Goetz et al., "MAPK Signal-integrating Kinase Controls Cap-independent Translation and Cell Type-specific Dyotoxicity of an Oncolytic Poliovirus," Molecular Therapy, Nov. 2010, vol. 18, No. 11, pp. 1937-1946.
Gromeier et al., "Oncolytic Poliovirus Immunotherapy of Primary CNS Tumors," Neuro-Oncology, Apr. 2013, vol. 15, Supplement No. 1, p. i20, Abstract No. 0077.

(Continued)

*Primary Examiner* — Shanon A. Foley
*Assistant Examiner* — Myron G Hill
(74) *Attorney, Agent, or Firm* — Banner & Witcoff, Ltd.

(57) ABSTRACT

Human clinical use of a chimeric poliovirus construct has demonstrated excellent anti-tumor effect. The mechanism of action is believed to involve both viral oncolysis as well as immune recruitment, both of which lead to necrosis in the area of the tumor. No adverse effects have been observed.

25 Claims, 5 Drawing Sheets

(56) References Cited

OTHER PUBLICATIONS

Merrill et al., "Poliovirus receptor CD155-targeted oncolysis of glioma," Neuro-Oncology, Jul. 2004, vol. 6, No. 3, pp. 208-217.
Anonymous: "View of NCT01491893 on Oct. 9, 2012," ClinicalTrials. gov Archive, Oct. 9, 2012, pp. 1-7.
De Stasio et al., "Gadolinium in Human Glioblastoma Cells for Gadolinium Neutron Capture Therapy," Cancer Research 61, May 15, 2001, pp. 4272-4277.
Extended European Search Report for related Application No. 13856989.2, dated Apr. 22, 2016, 12 pages.
Sampson MD. et al., "Co-localization of gadolinium-DTPA with high molecular weight molecules after intracerebral convection-enhanced delivery in man," Neurosurgery, Sep. 2011, 69(3), pp. 668-676.
Translated Notice of Reasons for Rejection for related Japanese Application No. 2015-544130, dispatched May 9, 2016, 4 pages.
Wollmann MD et al., "Oncolytic Virus Therapy of Glioblastoma Multiforme—Concepts and Candidates," Cancer J., 2012, 18(1) pp. 69-81.
Gromeier et al. "Internal ribosomal entry site substitution eliminates neurovirulence in intergeneric poliovirus Yecombinants" PNAS, vol. 93, pp. 2370-2375, Mar. 1996.
Office Action dated Oct. 9, 2017 in related Japanese Application No. 201380070749.7.
Ochiai et al. "Targeted Therapy for Glioblastoma Multiforme Neoplastic Meningitis with Intrathecal Delivery of an Oncolytic Recombinant Poliovirus," Clinical Cancer Research 2006; 12(4) pp. 1349-1354.
Notice of Reasons for Rejection issued in related Japanese Application No. 2017-084158, dated Jun. 18, 2018.
Desjardins et al., "Recurrent Glioblastoma Treated with Recombinant Poliovirus," The New England Journal of Medicine, published Jun. 26, 2018 at NEJM.org, along with attached appendix.
Aug. 30, 2018—(JP) Office Action—App 2015-544130—Eng Tran.
Melcher et al. "Thunder and Lightning: Immunotherapy and Oncolytic Viruses Collide," Molecular Therapy, Jun. 6, 2011.
Chen et al. "CV706, a Prostate Cancer-specific Adenovirus Variant, in Combination with Radiotherapy Produces Synergistic Antitumor Efficacy without Increasing Toxicity," Cancer Research, Jul. 15, 2001.
Jul. 4, 2018—(EP) Letters Patent granted in related EP application No. 13856989.2.
Park et al. "Scale to Predict Survival After Surgery for Recurrent Glioblastoma Multiforme" Journal of Clinical Oneology, vol. 28, No. 24, Aug. 20, 2010.
Pope et al. "Apparent diffusion coefficient histogram analysis stratifies progression-free and overall survival in patients with recurrent GBM treated with bevacizumab: a multi-center study" J Neurooncol. (2012) 108:491-498.
Kunwar et al. "Phase III randomized trial of CED of IL13-PE38QQR vs Gliadel wafers for recurrent glioblastoma" Neuro-Oncology 12(8):871-881, 2010.
Quinn et al. "Phase II Trial of Temozolomide Plus 06-Benzylguanine in Adults with Recurrent, Temozolomide-Resistant Malignant Glioma" Journal of Clinical Oncology, vol. 27, No. 8, Mar. 10, 2009.
Vredenburgh et al. "Bevacizumab Plus Irinotecan in Recurrent GLioblastoma Multiforme" Journal of Clinical Oncology; vol. 25; No. 30; Oct. 20, 2007.
Wick et al. "Phase III Study of Enzastaurin Compared with Lomustine in the Treatment of Recurrent Intracranial Glioblastoma" Journal of Clinical Oncology; vol. 28; No. 7; Mar. 1, 2010.

Friedman et al. "Bevacizumab Alone and in Combination with Irinotecan in Recurrent Glioblastoma" Journal of Clinical Oncology; vol. 27; No. 28; Oct. 1, 2009.
Reardon et al. "Randomized Phase III Study of Cilengitide, and Integrin-Targeting Arginine-Glycine-Aspartic Acid Peptide, in Recurrent Glioblastoma Multiforme" Journal of Clinical Oncology; vol. 26; No. 34; Dec. 1, 2008.
Desjardins et al. "Bevacizumab and Daily Temozolomide for Recurrent Glioblastoma" Cancer; 2012; 118(5):1302-1312.
Reardon et al. "Phase II Study of Imatinib Mesylate Plus Hydroxyurea in Adults with Recurrent Glioblastoma Multiforme" Journal of Clinical Oncology; vol. 23; No. 36; Dec. 20, 2008.
Batchelor et al. "Phase III Randomized Trial Comparing the Efficacy of Cediranib as Monotherapy, and in Combination with Lomustine, Versus Lomustine Alone in Patients with Recurrent Glioblastoma" Journal of Clinical Oncology; vol. 31; No. 26; Sep. 10, 2013.
Faal et al. "Single-agent bevacizumab or lomustine versus a combination of bevacizumab plus lomustine in patients with recurrent glioblastoma (BELOB trial): a randomised controlled phase 2 trial" Lancet Oncology; 2014:15:943-953.
Kreisl et al. "Phase II Trial of Single-Agent Bevacizumab Followed by Bevacizumab Plus Irinotecan at Tumor Progression in Recurrent Glioblastoma" Journal of Clinical Oncology; vol. 27; No. 5; Feb. 10, 2009.
Duerinck et al. "Randomized Phase II trial comparing axitinib with the combination of axitinib and lomustine in patients with recurrent glioblastoma" J. Neurooncol. (2018) 136:115-125.
Omuro et al. "Nivolumab with or without ipilimumab in patients with recurrent glioblastoma: results from exploratory phase I cohorts of CheckMate 143" Neuro-Oncology; 20(5); 674-686; 2018.
Ghiaseddin et al. "Phase II Study of Bevacizumab and Vorinostat for Patients with Recurrent World Health Organization Grade 4 Malignant Glioma" The Oncologist; 2018; 23:157-e21.
Lang et al. "Phase I Study of DNX-2401 (Delta-24-RGD) Oncolytic Adenovirus: Replication and Immunotherapeutic Effects in Recurrent Malignant Glioma" Journal of Clinical Oncology; vol. 36; No. 14; May 10, 2018.
May 18, 2020—(JP) Office Action—Appln. 2019-127280.
Masson et al. "Overexpression of the CD155 gene in human colorectal carcinoma" Gut; vol. 49; No. 2; Aug. 2001; pp. 236-240.
Nakai et al. "Overexpression of Necl-5 correlates with unfavorable prognosis in patients with lung adenocarcinoma" Cancer Science; May 2010; vol. 101; No. 5; pp. 1326-1330.
Ochiai et al. "Treatment of Intracerebral Neoplasia and Neoplastic Meningitis with Regional Delivery of Oncolytic Recombinant Poliovirus" Clinical Cancer Research; vol. 10; Jul. 15, 2004; pp. 4831-4838.
Gromeier et al. "Intergeneric poliovirus recombinants for the treatment of malignant glioma" PNAS; Jun. 6, 2000; Vol. 97; No. 12; pp. 6803-6808.
Solecki et al. "Expression of the Human Poliovirus Receptor/CD155 Gene Is Activated by Sonic Hedgehog" The Journal of Biological Chemistry; vol. 277; No. 28; Issue of Jul. 12, 2022; pp. 25697-25702.
Suzuki et al. "Exploration of Target Molecules for Prostate Cancer Gene Therapy" The Prostate; vol. 67; Issue 11; Aug. 1, 2007; pp. 1163-1173.
May 30, 2022—(JP) Notice of Reasons for Rejection—Appl No. 2021-059723—No English Translation.

\* cited by examiner

ONCOLYTIC POLIOVIRUS FOR HUMAN TUMORS

This invention was made using funds provided by the United States government. The U.S. government retains certain rights according to the terms of grants from the National Institutes of Health RO1 CA87537, P50 NS20023, RO1 CA124756, and RO1 CA140510.

TECHNICAL FIELD OF THE INVENTION

This invention is related to the area of anti-tumor therapy. In particular, it relates to oncolytic virus anti-tumor therapy.

BACKGROUND OF THE INVENTION

PVS-RIPO is an oncolytic poliovirus (PV) recombinant. It consists of the live attenuated type 1 (Sabin) PV vaccine containing a foreign internal ribosomal entry site (IRES) of human rhinovirus type 2 (HRV2). The IRES is a cis-acting genetic element located in the 5' untranslated region of the PV genome, mediating viral, $m^7G$-cap-independent translation.

PVS-RIPO oncolytic therapy has been reported in tissue culture assays (6, 7, 10, 15-17) and in animal tumor models, but not in clinical trials in humans. Because of the differences between tissue culture, animal models, and humans, efficacy is unpredictable. Moreover, viral preparations used in pre-clinical studies are often impure, so that any activity cannot be attributed to the agent under investigation.

The art provides no examples of oncolytic viral agents in which biological activity in tumor models correctly predicted efficacy in patients. The reason for this is that oncolytic viral therapy is the result of a complex, triangular relationship between (a) the infected malignant cells, (b) the non-malignant tumor microenvironment, and (c) the host immune system. A system of such complexity and intricacy has not been recreated in any animal model.

There is a continuing need in the art to identify and develop effective anti-cancer treatments for humans, particularly for patients with brain tumors.

SUMMARY OF THE INVENTION

According to one aspect of the invention a method is provided for treating a human harboring a solid tumor which expresses NECL5 (CD155, HVED, Nec1-5, PVS, TAGE4; nectin-like 5; nectin-like protein 5). A chimeric poliovirus construct is administered directly to the tumor in the human. The chimeric poliovirus comprises a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame.

These and other embodiments, which will be apparent to those of skill in the art upon reading the specification, provide the art with methods of treating tumors, including brain tumors.

BRIEF DESCRIPTION OF THE DRAWINGS

FIG. 1A. Tumor volumes upon mock (□) or PVS-RIPO (■) treatment. FIG. 1B. Average virus recovery from tumors at the indicated intervals.

DETAILED DESCRIPTION OF THE INVENTION

Figures 1A, 1B:
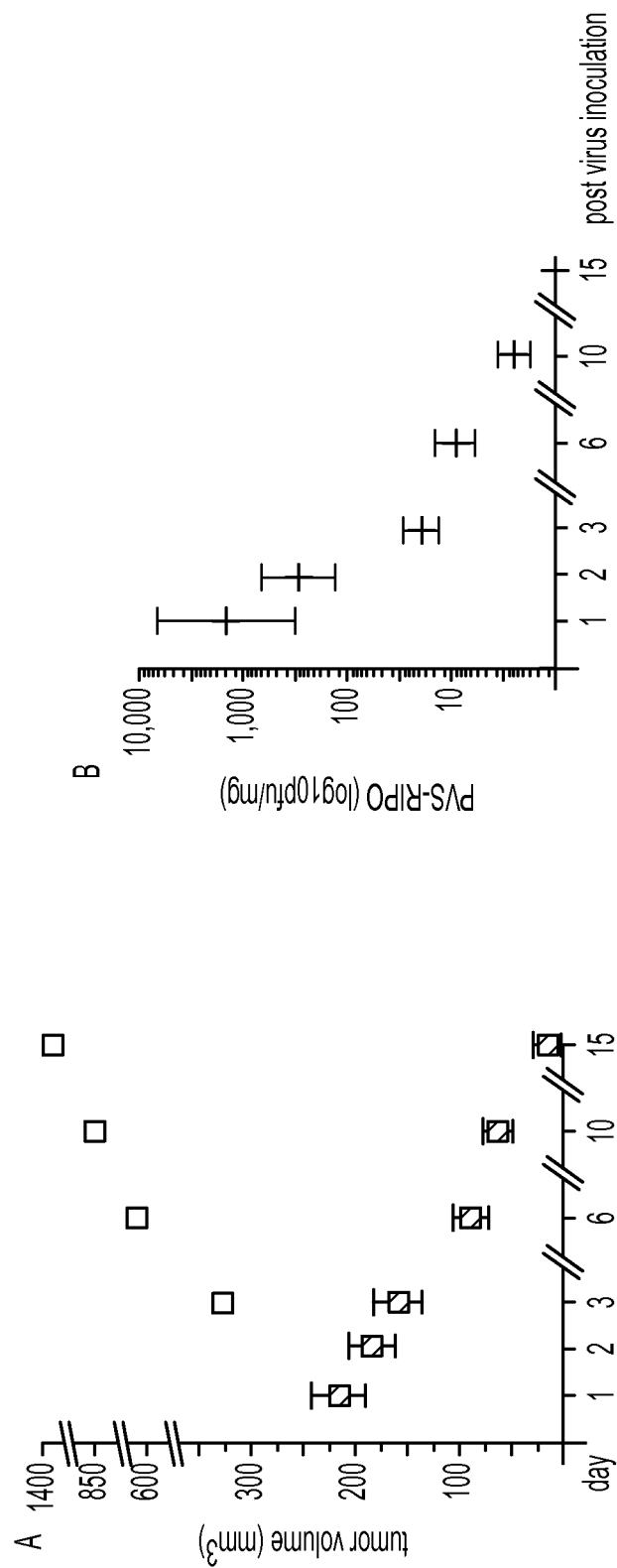
FIG. 1A-1B Intratumoral PVS-RIPO infusion induces gradual tumor regress.

The inventors have developed a viral construct for use in humans. Previously, laboratory grade preparations of the viral construct have been tested in cell culture and in animal models. But these tests are not sufficient to attribute any effect to the viral construct itself, rather than other elements in the crude, laboratory grade preparations. Moreover, as is well known in the art, cell culture and animal models are not predictive of efficacy in humans.

Because the poliovirus is a potential disease agent, extra precautions must be taken to ensure that disease-causing agents are not introduced to the subjects. Using good manufacturing procedures and purifications, a preparation was made that was sufficiently pure to permit introduction into humans in a trial.

Any technique for directly administering the preparation to the tumor may be used. Direct administration does not rely on the blood vasculature to access the tumor. The preparation may be painted on the surface of the tumor, injected into the tumor, instilled in or at the tumor site during surgery, infused into the tumor via a catheter, etc. One particular technique which may be used is convection enhanced delivery.

Any human tumor can be treated, including both pediatric and adult tumors. The tumor may be in any organ, for example, brain, prostate, breast, lung, colon, and rectum, Various types of tumors may be treated, including, for example, glioblastoma, medulloblastomas, carcinoma, adenocarcinoma, etc. Other examples of tumors include, adrenocortical carcinoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, breast sarcoma, bronchial cancer, bronchoalveolar carcinoma, cervical cancer, craniopharyngioma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gall bladder cancer, gastric cancer, gastrointestinal carcinoid tumor, gastrointestinal stromal tumor, gestational trophoblastic tumor, gestational trophoblastic tumor, glioma, head and neck cancer, hepatocellular cancer, Hilar cholangiocarcinoma, hypopharyngeal cancer, intraocular melanoma, islet cell tumor, Kaposi sarcoma, Langerhans cell histiocytosis, large-cell undifferentiated lung carcinoma, laryngeal cancer, lip cancer, lung adenocarcinoma, malignant fibrous histiocytoma, medulloepithelioma, melanoma, Merkel cell carcinoma, mesothelioma, endocrine neoplasia, nasal cavity cancer, nasopharyngeal cancer, neuroblastoma, oral cancer, oropharyngeal cancer, osteosarcoma, ovarian clear cell carcinoma, ovarian epithelial cancer, ovarian germ cell tumor, pancreatic cancer, papillomatosis, paranasal sinus cancer, parathyroid cancer, penile cancer, pharyngeal cancer, pineal parenchymal tumor, pineoblastoma, pituitary tumor, pleuropulmonary blastoma, renal cell cancer, respiratory tract cancer with chromosome 15 changes, retinoblastoma, rhabdomyosarcoma, salivary gland cancer, small cell lung cancer, small intestine cancer, soft tissue sarcoma, squamous cell carcinoma, squamous non-small cell lung cancer, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, and Wilms tumor.

Optionally, patients may be stratified on the basis of NECL5 expression. This can be assayed at the RNA or protein level, using probes, primers, or antibodies, for example. The NECL5 expression may guide the decision to treat or not treat with the chimeric poliovirus of the present invention. The NECL5 expression may also be used to guide the aggressiveness of the treatment, including the dose, frequency, and duration of treatments.

Treatment regimens may include, in addition to delivery of the chimeric poliovirus construct, surgical removal of the tumor, surgical reduction of the tumor, chemotherapy, biological therapy, radiotherapy. These modalities are standard of care in many disease states, and the patient need not be denied the standard of care. The chimeric poliovirus may be administered before, during, or after the standard of care. The chimeric poliovirus may be administered after failure of the standard of care.

Applicants have found that the clinical pharmaceutical preparation of the chimeric poliovirus has admirable genetic stability and homogeneity. This is particularly advantageous as the poliovirus is known to be highly mutable both in culture and in natural biological reservoirs. Any suitable assay for genetic stability and homogeneity can be used. One assay for stability involves testing for the inability to grow at 39.5 degrees C. Another assay involves bulk sequencing. Yet another assay involves testing for primate neurovirulence.

While applicants do not wish to be bound by any particular mechanism of action, it is believed that multiple mechanisms may contribute to its efficacy. These include lysis of cancer cells, recruitment of immune cells, and specificity for cancer cells. Moreover, the virus is neuroattenuated.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Animal Tumor Models.

An IND-directed efficacy trial of PVS-RIPO was conducted in the HTB-15 GBM xenograft model in athymic mice. PVS-RIPO (from the clinical lot) was administered at the 'mouse-adjusted', FDA-approved max. starting dose [the FDA-approved max. starting dose (10e8 TCID) was adjusted for the reduced tumor size in mice (to 6.7×10e6 TCID)]. Delivery mimicked the intended clinical route, i.e., slow intratumoral infusion. Under these conditions, PVS-RIPO induced complete tumor regress in all animals after 15 days (FIG. 1A). While virus was recovered from treated tumors until day 10, the levels were modest at best, indicating that direct viral tumor cell killing alone cannot account for the treatment effect (FIG. 1B).

Evidence from animal tumor models suggests that intratumoral inoculation of PVS-RIPO causes direct virus-induced tumor cell killing and elicits a powerful host immunologic response against the infected/killed tumor (3, 7, 10). The response to virus infusion is characterized by a strong, local inflammatory response, leading to immune infiltration of the tumor. Eventually the slow tissue response to PVS-RIPO infusion leads to the demise of the tumor mass and its replacement by a scar.

Example 2

Clinical Trials.

IND no. 14,735 'Dose-finding and Safety Study of PVSRIPO Against Recurrent Glioblastoma' was FDA-approved on Jun. 19, 2011 and IRB-approved on Oct. 27, 2011. A phase I/II clinical trial in patients with recurrent glioblastoma (GBM) (NCT01491893) is currently enrolling patients.

Two human subjects have so far been treated with PVS-RIPO per IRB-approved protocol. Preliminary findings from the first subject are described in Example 3.

Example 3

Preliminary Findings with First Human Subject.

The patient is a 21-year-old female nursing student diagnosed with a right frontal GBM (WHO grade IV). She was first diagnosed in 06/2011, at the age of 20 years, following a history of severe headaches and unsuccessful treatment for a suspected sinus infection. Brain imaging was obtained on Jun. 17, 2011 and showed a large right frontal mass, measuring ~5×6 cm. She underwent a subtotal resection of the right frontal mass on Jun. 22, 2011, with pathology confirming GBM (WHO grade IV). Given the young age of the patient, her excellent performance status and the subtotal tumor resection, it was decided to treat her aggressively with a combination of six weeks of radiation therapy with concurrent Temodar chemotherapy at 75 mg/m$^2$ by mouth daily and bevacizumab (antiangiogenic agent) administered every 2 weeks. The patient completed six weeks of treatment on Sep. 18, 2011. On Oct. 3, 2011, the patient initiated adjuvant therapy with monthly, five-day Temodar chemotherapy in addition to bevacizumab 10 mg/kg every two weeks.

Figure 2:
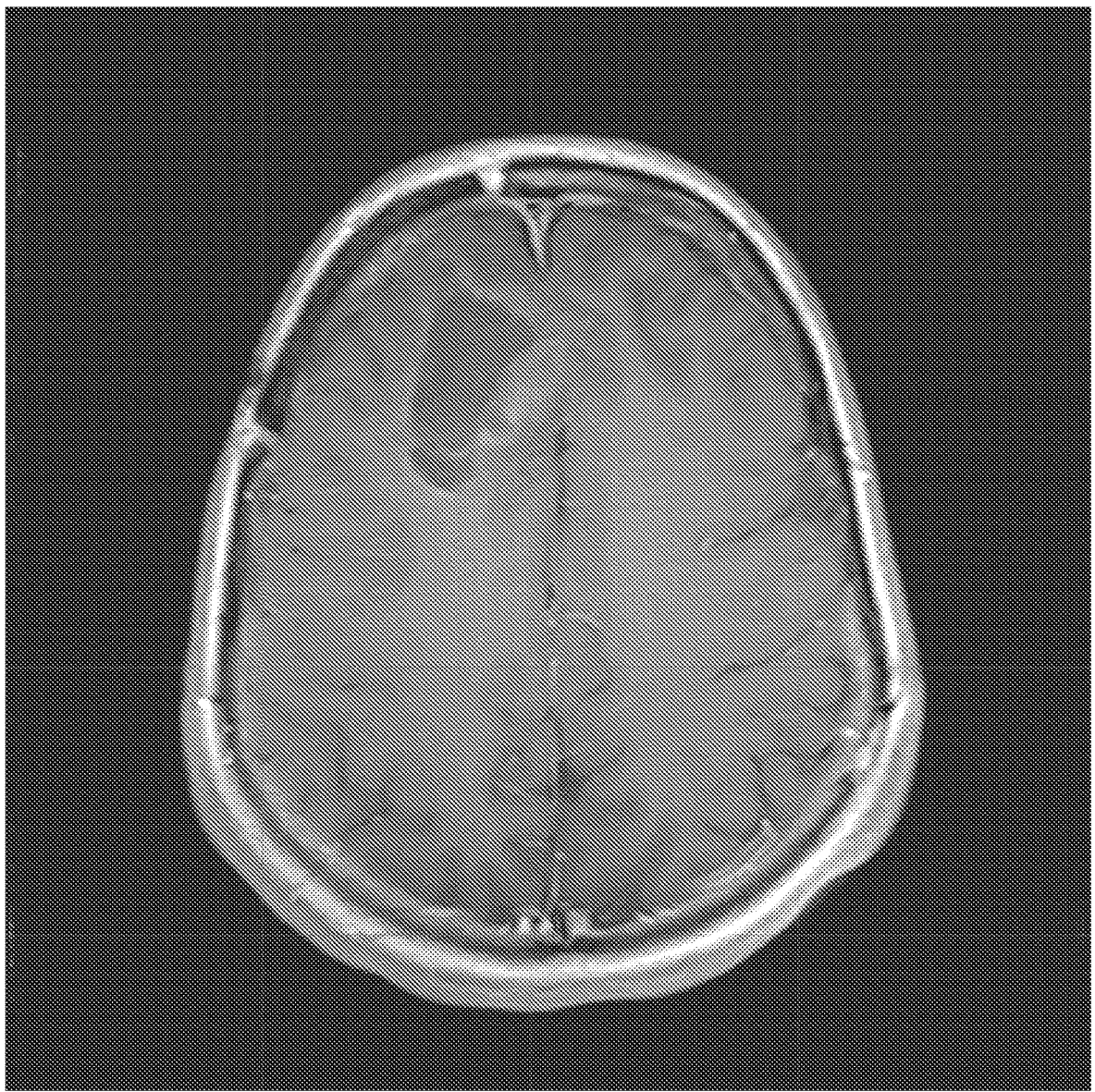
FIG. 2. MRI from Apr. 16, 2012. Axial, postcontrast, T1-weighted MRI showing disease progression.
Figure 3:
FIG. 3. MRI from May 9, 2012. Axial, postcontrast, T1-weighted MRI obtained pre-infusion of PVS-RIPO.
Figure 4:
FIG. 4. MRI from May 11, 2012. Axial, postcontrast, T1-weighted MRI showing distribution of Gd-DTPA contrast and—presumably—PVS-RIPO within the brain.
Figure 5:
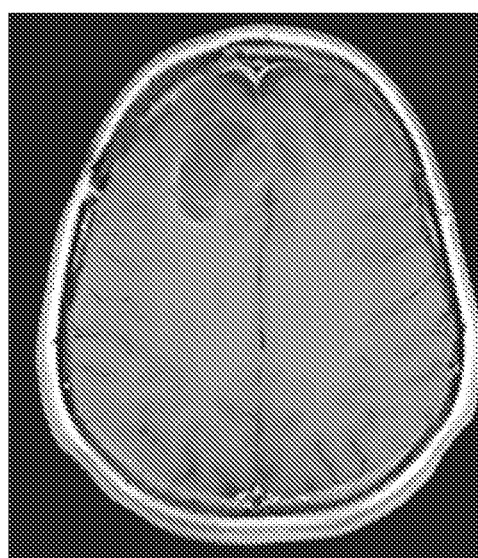
FIG. 5. MRI from Jun. 6, 2012. Axial, postcontrast, T1-weighted MRI showing disease stability.
Figure 6:
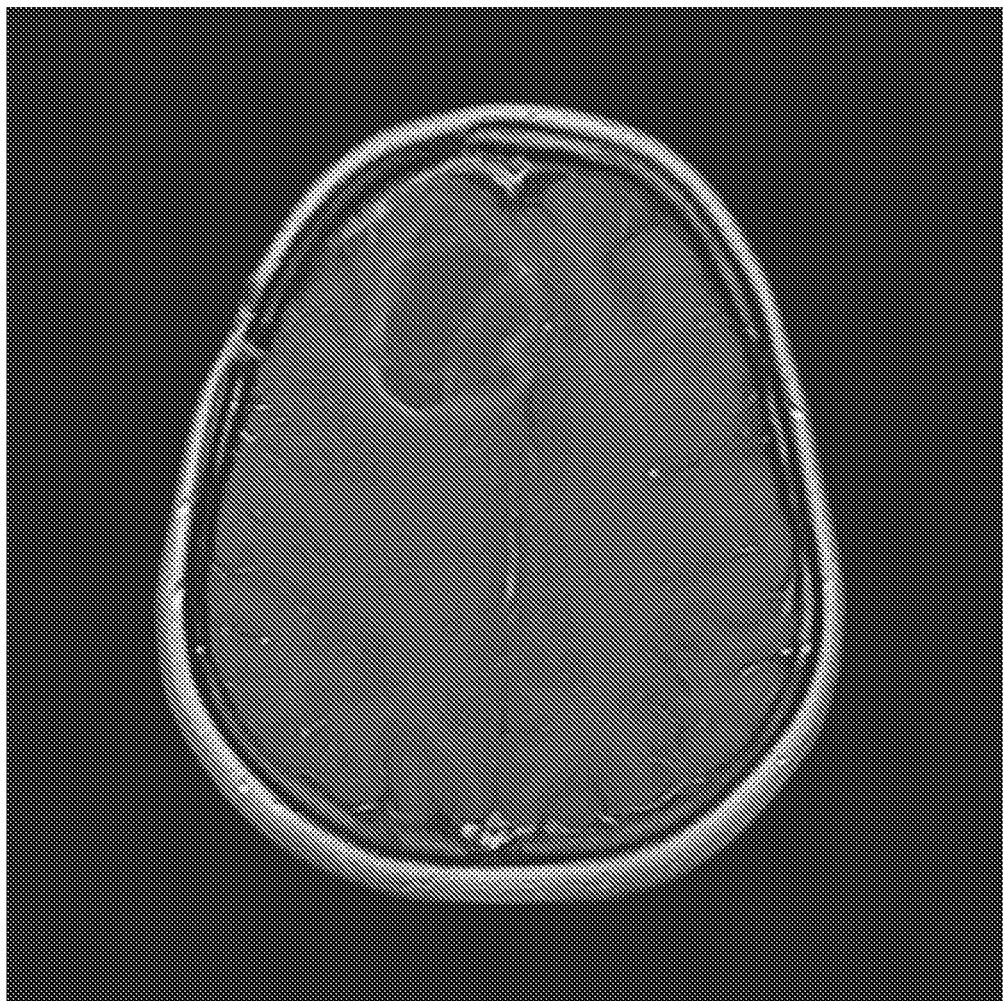
FIG. 6. MRI from Jul. 9, 2012. Axial, postcontrast, T1-weighted MRI revealed concerns for disease progression.

On Apr. 16, 2012, the patient presented to clinic after having experienced her first generalized seizure, which occurred in her sleep. By that time, she had completed six months of the combination of Temodar and bevacizumab. She had attributed the seizure to increased stress at school, as she was completing a degree to become a pediatric oncology nurse, despite her diagnosis of GBM and ongoing chemotherapy treatment. The brain MRI obtained on that day showed tumor recurrence, with a new nodular enhancement along the medial aspect of the resection cavity (FIG. 2).

The patient was offered multiple treatment options, but elected to pursue the PVS-RIPO clinical trial. Following her first generalized seizure, she was initiated on Keppra, but forgot to take it on occasion and because of this and the known tumor recurrence, the patient experienced a second generalized seizure in her sleep on May 7, 2012. She went back to her baseline neurologic condition and was worked up to enroll on protocol.

A follow-up MRI was obtained on May 9, 2012 (FIG. 13), before the patient underwent infusion of PVS-RIPO on May 11, 2012 with the FDA-approved max. starting dose (10e8) by the intended clinical delivery method (convection-enhanced, intratumoral infusion of 3 mL of virus suspension containing the contrast Gd-DTPA over 6 hrs; see Example 4) and experienced no neurologic or other complications related to this.

An MRI obtained immediately after completion of the infusion documents the distribution of the infusate (FIG. 14).

Our research team followed up on the patient on a weekly basis and she was seen in clinic two weeks post infusion, at which time she denied any new neurologic symptoms, seizure recurrence, fatigue, shortness of breath or weakness. She again was evaluated in clinic on Jul. 7, 2012 and her physical and neurological conditions remained normal. The brain MRI obtained at that visit showed stability of the disease (FIG. 15).

The patient was seen in clinic on Jul. 9, 2012. Once more, she denied any new neurologic symptoms, including the absence of any recurrent seizure activity since the seizure observed on May 6, 2012, prior to PVS-RIPO infusion. She also reported that her mood was good, that she was content with her progress in nursing school, feeling that she is able to focus in school much better since after her infusion. She was also excited by her move with two roommates and by the fact that she is able to exercise regularly. Her brain MRI obtained on that day showed a slightly increased mass effect and minimal increase in superior linear enhancement, concerning for progression of disease (FIG. 16).

Figure 7:
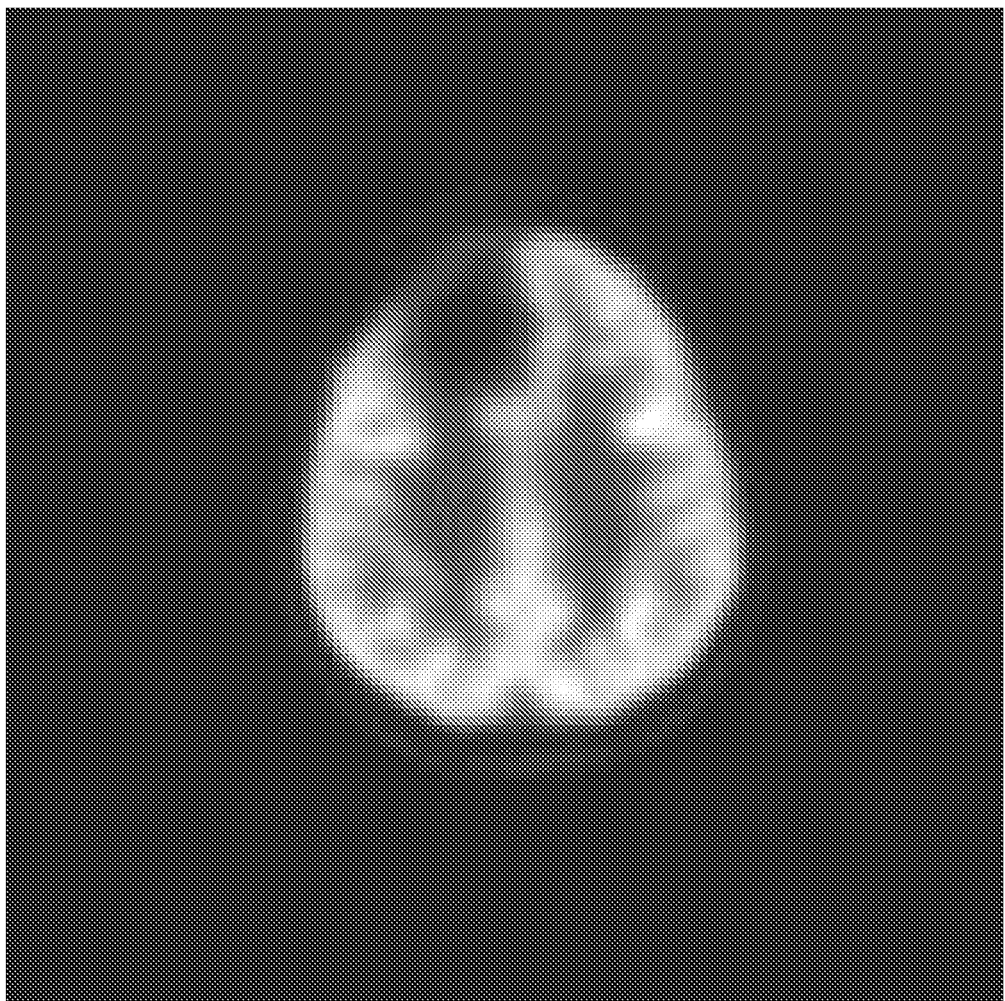
FIG. 7 (formerly FIG. 17). 18-FDG PET scan from Jul. 11, 2012. The results suggest the absence of hypermetabolic activity in the area of concern on MRI.

In view of worrisome radiographic changes with no clinical worsening, we decided to obtain an 18-FDG PET scan. The 18-FDG PET scan demonstrated hypometabolic activity in the area of concern on the MRI, suggestive of a necrotic process (treatment response effect; FIG. 7). The PET scan from 07/09 suggests the absence of viable tumor. After discussion with the patient and her mother, it was decided to continue to follow the patient from a clinical and radiographic standpoint.

In check-ups on 8/27 and 10/22 the patient denied any new neurologic symptoms, including the absence of any seizure activity since the seizure on Jun. 6, 2012 (prior to PVS-RIPO infusion). The patient reports improved cognitive/memory function, motor function (exercise). As of 10/26, the patient is neurologically normal.

Because of the favorable radiographic presentation at 08/27, a PET scan was not ordered. The patient was re-scanned on 10/22 and there was a quantifiable radiographic response.

An MRI/PET overlay demonstrates the absence of signal from the general area of the tumor recurrence.

Example 4

Convection Infusion.

Preoperatively the BrainLab iPlan Flow system is used to plan catheter trajectories based on predicted distributions using information obtained from a preoperative MRI.

This invention uses one mM of gadolinium, along with $^{124}$I-labeled human serum albumin to a surrogate tracer to identify the distribution of the poliovirus. This could be used for other drug infusions as well. The gadolinium and radio-labeled albumin is co-infused with the drug and various MRI sequences and PET imaging are used to quantify the distribution.

The entire volume of the agent to be delivered will be pre-loaded into a syringe by the investigational pharmacist and connected to the catheter under sterile conditions in the operating room or the NICU just prior to beginning of infusion. Due to the complexity of scheduling all of the necessary components for the infusion (operating room time, pharmacy time, and radiology appointments), a +1 day window has been built in to the study for the study drug infusion. This means that the infusion is allowed to start the following day after the biopsy/catheter placement. This will still be considered "day 0" in regards to the protocol and the timing of the subsequent events. At the time of virus injection, emergency drugs, including epinephrine and diphenhydramine will be available and the neurologic status, oxygen saturation, and cardiac rhythm will be monitored. Drug infusion will occur in the Neuro-Surgical Intensive Care Unit (NSCU) so that all other emergency facilities will be available. Patients will be treated with a prophylactic antibiotic such as nafcillin, a second-generation cephalosporin or vancomycin starting with the induction of anesthesia for the catheter placement.

Based on our own experience, previously published reports (19) and IRB- and FDA-approved trials using similar infusion techniques (IRB #4774-03-4R0), patients will be infused at a rate of 500 µL/hr. A Medfusion 3500 infusion pump will be pre-programmed to a delivery rate of 500 µL/hr. The agent (which will be in a total volume of 10 mL to account for 'dead-space' of 3.3723 mL in the infusion system) will be loaded in a 20 mL syringe into the syringe pump at the initial onset to avoid any interruptions in the infusion. The total amount of the inoculum delivered to the patient will be 3 mL. The catheter itself (30 cm length, 1 mm interior diameter) cannot be preloaded with virus suspension. Therefore, the initial ~250 µL of infusion will be preservative-free saline in the 'dead-space' of the indwelling catheter. To account for this, the infusion pump will be programmed for delivery of 3.250 mL. The infusion will be performed using a Medfusion 3500 (Medex, Inc., Duluth, Ga.) syringe infusion pump. The virus injection procedure will be completed within 6.5 hrs. The catheter will be removed immediately following the delivery of PVSRIPO.

The infusion catheter (PIC 030) and infusion tubing (PIT 400) will be supplied by Sophysa, Inc. (Crown Point, Ind.). The Infusion Catheter Kit is a 30 cm clear, open-ended catheter (1.0 mm ID/2.0 mm OD) with 1 cm markings for 20 cm. The catheter comes with a 30 cm stainless steel stylet, a barbed female luer lock with cap and a stainless steel trocar. The Infusion Tubing Kit consists of a 3-way stopcock connector with air filter, 4 m of microbore tubing with antisiphon valve, a red, vented cap and a white luer lock cap. The catheter products are packaged sterile and non-pyrogenic and are intended for single (one-time) use only. The infusion will be performed using a Medfusion 3500 (Medex, Inc. Duluth, Ga.) syringe infusion pump.

REFERENCES

The disclosure of each reference cited is expressly incorporated herein.

1. Castriconi R, A Daga, A Dondero, G Zona, P L Poliani, et al. 2009. NK cells recognize and kill human glioblastoma cells with stem cell-like properties. J Immunol 182:3530-39.

2. de Breyne S, Y Yu, A Unbehaun, T V Pestova, C U Hellen. 2009. Direct functional interaction of initiation factor eIF4G with type 1 internal ribosomal entry sites. Proc Natl Acad Sci USA 106:9197-202.
3. Dobrikova E Y, T Broadt, J Poiley-Nelson, X Yang, G Soman, et al. 2008. Recombinant oncolytic poliovirus eliminates glioma in vivo without genetic adaptation to a pathogenic phenotype. Mol Ther 16:1865-72.
4. Dobrikova E Y, C Goetz, R W Walters, S K Lawson, J O Peggins, et al. 2012. Attenuation of neurovirulence, biodistribution, and shedding of a poliovirus:rhinovirus chimera after intrathalamic inoculation in *Macaca fascicularis*. J Virol 86:2750-9.
5. Erickson B M, N L Thompson, D C Hixson. 2006. Tightly regulated induction of the adhesion molecule nec1-5/CD155 during rat liver regeneration and acute liver injury. Hepatology 43:325-34.
6. Goetz C, E Dobrikova, M Shveygert, M Dobrikov, M Gromeier. 2011. Oncolytic poliovirus against malignant glioma. Future Virol 6:1045-58.
7. Goetz, C, R G Everson, L Zhang, M Gromeier. 2010. MAPK signal-integrating kinase controls cap-independent translation and cell type-specific cytotoxicity of an oncolytic poliovirus. Mol Ther 18:1937-46.
8. Gromeier M, L Alexander, E Wimmer. 1996. Internal ribosomal entry site substitution eliminates neurovirulence in intergeneric poliovirus recombinants. Proc Natl Acad Sci USA 93:2370-5.
9. Gromeier M, B Bossert, M Arita, A Nomoto, E Wimmer. 1999. Dual stem loops within the poliovirus internal ribosomal entry site control neurovirulence. J Virol 73:958-64.
10. Gromeier M, S Lachmann, M R Rosenfeld, P H Gutin, E Wimmer. 2000. Intergeneric poliovirus recombinants for the treatment of malignant glioma. Proc Natl Acad Sci USA 97:6803-8.
11. Gromeier M, D Solecki, D D Patel, E Wimmer. 2000. Expression of the human poliovirus receptor/CD155 gene during development of the central nervous system: implications for the pathogenesis of poliomyelitis. Virology 273:248-57.
12. Iwasaki A, R Welker, S Mueller, M Linehan, A Nomoto, et al. 2002. Immunofluorescence analysis of poliovirus receptor expression in Peyer's patches of humans, primates, and CD155 transgenic mice: implications for poliovirus infection. J Infect Dis 186:585-92.
13. Joshi S, S Kaur, A J Redig, K Goldsborough, K David, et al. 2009. Type I IFN-dependent activation of Mnk1 and its role in the generation of growth inhibitory responses. Proc Natl Acad Sci USA 106:12097-102.
14. Masson D, A Jarry, B Baury, P Blanchardie, C Laboisse, et al. 2001. Overexpression of the CD155 gene in human colorectal carcinoma. Gut 49:236-40.
15. Merrill M K, G Bernhardt, J H Sampson, C J Wikstrand, D D Bigner, et al. 2004. Poliovirus receptor CD155-targeted oncolysis of glioma. Neuro-oncol 6:208-17.
16. Merrill M K, E Y Dobrikova, M Gromeier. 2006. Cell-type-specific repression of internal ribosome entry site activity by double-stranded RNA-binding protein 76. J Virol 80:3147-56.
17. Merrill M K, M Gromeier. 2006. The double-stranded RNA binding protein 76:NF45 heterodimer inhibits translation initiation at the rhinovirus type 2 internal ribosome entry site. J Virol 80:6936-42.
18. Nakai R, Y Maniwa, Y Tanaka, W Nishio, M Yoshimura, et al. 2010. Overexpression of Nec1-5 correlates with unfavorable prognosis in patients with lung adenocarcinoma. Cancer Sci 101:1326-30.
19. Nepliouevа V, E Y Dobrikova, N Mukherjee, J D Keene, M Gromeier. 2010. Tissue type-specific expression of the DRBP76 and genome-wide elucidation of its target mRNAs. PloS One 5:e11710.
20. Ochiai H, S A Campbell, G E Archer, T A Chewning, E Dragunsky, et al. 2006. Targeted therapy for glioblastoma multiforme neoplastic meningitis with intrathecal delivery of an oncolytic recombinant poliovirus. Clin Can Res 12:1349-54.
21. Ochiai H, S A Moore, G E Archer, T Okamura, T A Chewning, et al. 2004. Treatment of intracerebral neoplasia and neoplastic meningitis with regional delivery of oncolytic recombinant poliovirus. Clin Can Res 10:4831-8.
22. Takai Y, J Miyoshi, W Ikeda, H Ogita. 2008. Nectins and nectin-like molecules: roles in contact inhibition of cell movement and proliferation. Nat Rev Mol Cell Biol 9:603-15.
23. Toyoda H, J Yin, S Mueller, E Wimmer, J Cello. 2007. Oncolytic treatment and cure of neuroblastoma by a novel attenuated poliovirus in a novel poliovirus-susceptible animal model. Cancer Res 67:2857-64.
24. Wahid R, M J Cannon, M Chow. 2005. Dendritic cells and macrophages are productively infected by poliovirus. J Virol 79:401-9.

We claim:

1. A method of treating a human harboring a solid tumor which expresses NECL5 (nectin-like protein 5), said method comprising the steps of:

administering directly to the solid tumor in the human a PVS-RIPO chimeric poliovirus construct comprising a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame, whereby the tumor is treated.

2. The method of claim 1 wherein convection enhanced delivery is used to administer the chimeric poliovirus construct.

3. The method of claim 1 wherein the solid tumor is a glioblastoma.

4. The method of claim 1 wherein the solid tumor is a prostate tumor.

5. The method of claim 1 wherein the solid tumor is a brain tumor and the administering is intracerebral.

6. The method of claim 1 wherein the solid tumor is a medulloblastoma.

7. The method of claim 1 wherein the solid tumor is a breast tumor.

8. The method of claim 1 wherein the solid tumor is a lung tumor.

9. The method of claim 1 wherein the solid tumor is a colorectal tumor.

10. The method of claim 1 wherein the solid tumor is a brain tumor and the administering is intracerebral infusion with convection enhanced delivery.

11. The method of claim 10 wherein the administering is stereotactically guided.

12. The method of claim 1 wherein the human is an adult.

13. The method of claim 1 wherein the human is a child.

14. The method of claim 12 wherein concurrent or serial chemotherapy is administered to the human.

15. The method of claim 13 wherein concurrent or serial radiotherapy is administered to the human.

16. The method of claim 1 wherein the solid tumor is subjected to surgical removal before or after administering the human chimeric poliovirus construct.

17. The method of claim 1 wherein prior to the step of administering the solid tumor is tested for expression of NECL5.

18. A method of treating a human harboring a solid tumor which expresses NECL5 (nectin-like protein 5), said method comprising the steps of:

testing a solid tumor to ascertain that it expresses NECL5; and administering directly to the tumor in the human a PVS-RIPO chimeric poliovirus construct comprising a Sabin type I strain of poliovirus with a human rhinovirus 2 (HRV2) internal ribosome entry site (IRES) in said poliovirus' 5' untranslated region between said poliovirus' cloverleaf and said poliovirus' open reading frame, wherein the administering is stereotactically guided, intracerebral infusion with convection enhanced delivery.

19. The method of claim 18 wherein the solid tumor is a glioblastoma.

20. The method of claim 18 wherein the solid tumor is a medulloblastoma.

21. The method of claim 1 wherein the solid tumor is a melanoma.

22. The method of claim 1 wherein the solid tumor is a head and neck squamous cell carcinoma (HSNCC).

23. The method of claim 1 wherein the solid tumor is an ovarian cancer.

24. The method of claim 1 wherein the solid tumor is a bladder cancer.

25. The method of claim 1 wherein the solid tumor is an esophageal cancer.

* * * * *

UNITED STATES PATENT AND TRADEMARK OFFICE
CERTIFICATE OF CORRECTION

| | |
|---|---|
| PATENT NO. | : 11,406,677 B2 |
| APPLICATION NO. | : 17/016699 |
| DATED | : August 9, 2022 |
| INVENTOR(S) | : Gromeier et al. |

It is certified that error appears in the above-identified patent and that said Letters Patent is hereby corrected as shown below:

In the Claims

Claim 22, Line 12-13:
Delete "squamous cell carcinoma (HSNCC)" and insert --cancer-- therefor.

Signed and Sealed this
Ninth Day of January, 2024

Katherine Kelly Vidal
*Director of the United States Patent and Trademark Office*